United States Patent [19]

Pinchak

[11] 4,301,809
[45] Nov. 24, 1981

[54] ESOPHAGEAL MONITORING APPARATUS

[76] Inventor: Alfred C. Pinchak, 19750 Fairmount Blvd., Shaker Hts., Ohio 44118

[21] Appl. No.: 130,074

[22] Filed: Mar. 13, 1980

[51] Int. Cl.$^3$ .............................................. A61B 5/02
[52] U.S. Cl. .................................. 128/695; 128/715; 128/782
[58] Field of Search .......................... 73/404, 488–489, 73/493, 495, 503, 505; 128/349 R, 349 B, 349 BV, 670–675, 695, 701, 713–715, 748, 773–774, 780, 782; 179/15 T

[56] References Cited

U.S. PATENT DOCUMENTS

| | | | |
|---|---|---|---|
| 2,837,082 | 6/1958 | Elliott et al. | 128/668 |
| 3,480,003 | 11/1969 | Crites | 128/715 |
| 3,499,434 | 3/1970 | Ullrich et al. | 128/670 |
| 3,499,435 | 3/1970 | Rockwell et al. | 128/671 |
| 3,695,253 | 10/1972 | Vielhauer | 128/695 |
| 3,939,823 | 2/1976 | Kaye et al. | 128/748 |
| 3,951,136 | 4/1976 | Wall | 128/670 |
| 4,176,660 | 12/1979 | Mylrea et al. | 128/715 |
| 4,198,990 | 4/1980 | Higgins et al. | 128/782 |

OTHER PUBLICATIONS

George, M. et al., "Measurement of Max. Rate of Rise of Aortic BP", Med. Res. Engrg., Fourth Quarter, 1967, pp. 21–24.
Verburg, J. et al., "Phaseless Recursive Filtering Applied to Chest Wall Disp. and Vel. Using Accelerometers", MBE, vol. 12 #4, Jul. 1974, pp. 483–488.
Mounsey, P., "Precordial Ballistocardiography", Brit. Heart Jrnl., vol. 19, pp. 259–271 (1957).
Rosa, L. M. et al., "LF Tracings of Precordial Displacement and Acceleration", Amer. Jrnl. Cardiology, pp. 669–674, (Nov. 1959).
Rosa, L. M. et al., "The Precordial Accelerogram in Normal Subjects and Non-Cardiac Patients", Exper. Med. Surgery, vol. 19, pp. 207–222 (1961).
Bew, F. E. et al., "'Pixie' Cardiography—Accelerometer Applications to Phonocardiography and Displacement Cardiography in Childhood", Brit. Ht. Jrnl., vol. 33, pp. 702–706 (1971).
Reuben, S. R. et al., "Precordial Accelerometry: An Indirect Assessment of Left Ventricular Performance", Europ. Jrnl. of Clinical Investig., vol. 3, pp. 324–330 (1973).
Talakov, A. A., "Seismog. Invest. in Man & Exper. Animals", Proc. of Europ. Cong. of Ballisto-Cardiography, Ljubljana (1971) pt. II: Biom. Sci. & CV Dynamics, Bibl. Cardiol, vol. 31, pp. 136–140 (Karger, Basel 1973).
Manley, M. T. et al., "Aspects of Non-Invasive Cardiac Monitoring", Biomed. Engrg., pp. 144–148 (Apr. 1974).

Primary Examiner—Robert W. Michell
Assistant Examiner—Francis J. Jaworski
Attorney, Agent, or Firm—Fay & Sharpe

[57] ABSTRACT

This application discloses an esophageal stethoscope for audibly and electronically monitoring a patient's cardiovascular functions. The stethoscope comprises a flexible tube which is dimensioned to be disposed in the patient's esophagus. Adjacent one end of the tube are a plurality of apertures covered by a thin membrane which allow acoustic waves to enter the tube. The other end of the tube is connected with ear pieces to allow the operator to hear the sounds received at the other end of the tube. Also disposed in the one end of the tube is an accelerometer or other electrokinetic transducer. The accelerometer is connected with a circuit for applying an excitation voltage to the accelerometer so that an analog signal is produced which varies with the acceleration of the accelerometer. A visual display is produced from the analog signal. A computer may operate on the analog signal with various algorithms to produce displays of different cardiovascular functions.

15 Claims, 1 Drawing Figure

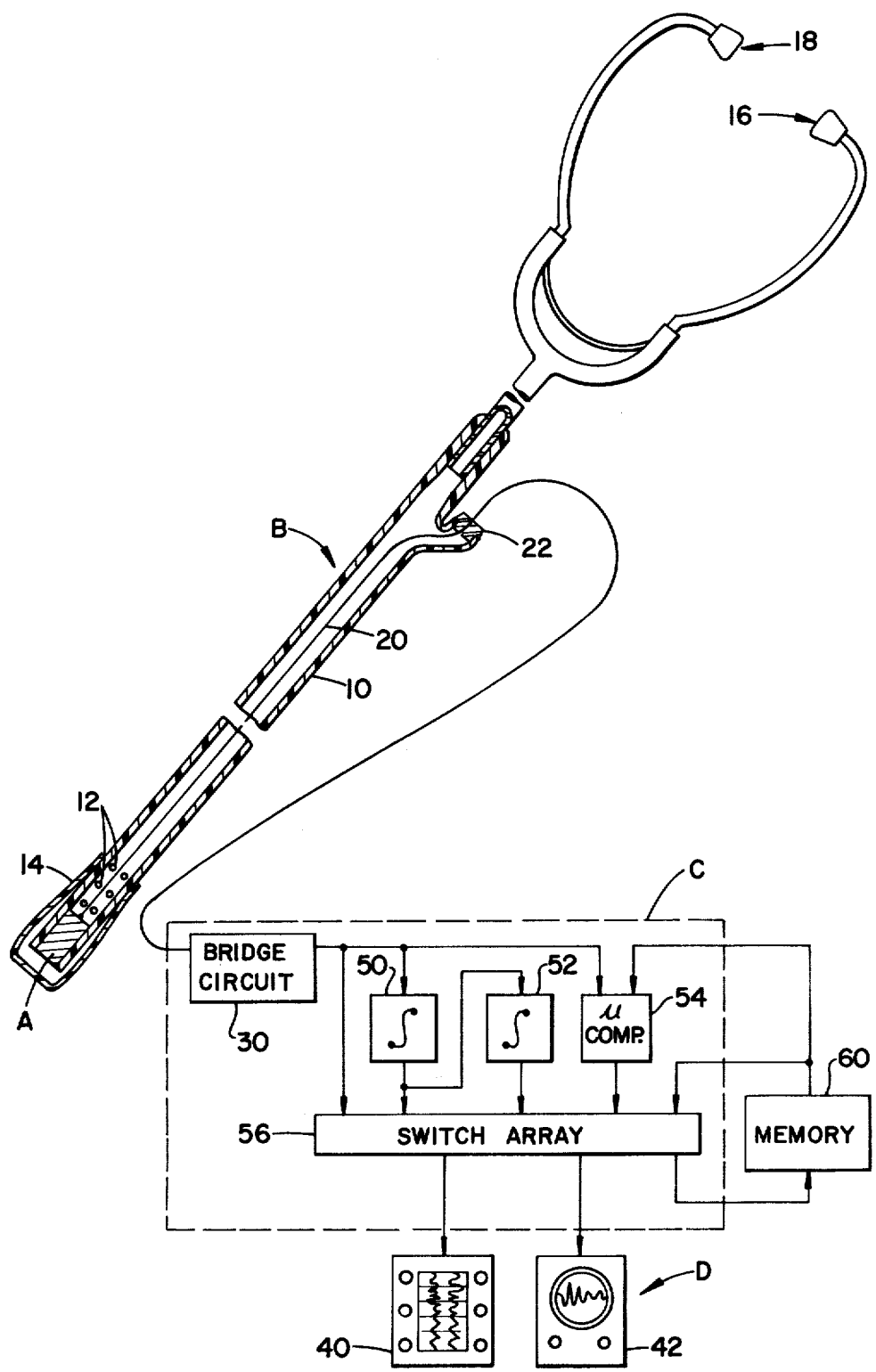

ESOPHAGEAL MONITORING APPARATUS

BACKGROUND OF THE INVENTION

This application pertains to the art of medical diagnostic apparatus and more particularly to noninvasive measurement of cardiac functions. The invention is particularly amenable to combination with an esophageal stethoscope and will be described with particular reference to this combination. However, it will be appreciated that the invention has broader aspects. For example, the invention may be utilized independent of any audio esophageal stethoscope, or in combination with other monitoring apparatus. Further, the present invention may be disposed in other body passages for noninvasive measurement of cardiac or other physiological functions.

In the past, precordial stethoscopes, seismometers and accelerometers have all been used to monitor cardiac and other physiological functions from the exterior of the patient. Precordial and esophageal stethoscopes have been used for audibly monitoring patients' cardiac functions. However, cardiac motion produces energy and also provides information at frequencies below the threshold of human hearing. Moreover, simple precordial and esophageal stethoscopes produce no electrical signals. Accordingly, this acoustic information is not readily converted to a visual display, recorded, or processed to extract more sophisticated significance from the information. In the past, esophageal stethoscopes have been combined with electronic detectors such as thermistors for monitoring temperature or pressure transducers for monitoring esophageal motility. However, these electronic devices generally measure different and additional physiological parameters than the stethoscope.

One of the problems with the prior art of precordial and esophageal stethoscopes is that they are unsuited for monitoring data at frequencies below the audio frequency range. Another problem has been the inability to record or process the information monitored.

The prior art has lacked a noninvasive apparatus for internally measuring cardiovascular acceleration, velocity, or displacement produced by the cardiovascular system.

The present invention contemplates a new and improved noninvasive cardiovascular monitoring apparatus which overcomes the above-referenced problems and others. The present invention provides an accurate cardiac monitoring apparatus which is relatively easy to use, relatively inexpensive, and readily adaptable for use in conjunction with commonly used medical apparatus. In accordance with the present invention there is provided an esophageal cardiovascular monitoring apparatus. The apparatus includes an electrokinetic transducer for generating electrical signals which are indicative of its movement. The electrokinetic transducer is adapted to be disposed within the esophagus of the patient generally adjacent the patient's heart. The apparatus further includes an esophageal positioning means for selectively positioning the electrokinetic transducer in the patient's esophagus. Electrically connected with the electrokinetic transducer is a representation producing means for producing a representation which is indicative of a function of the movement of the electrokinetic transducer.

In accordance with a more limited aspect of the invention there is provided an esophageal stethoscope for audibly and electronically monitoring a function of the cardiovascular system of a patient. The stethoscope includes a flexible tube adapted to be disposed within the patient's esophagus. Disposed adjacent one end of the tube there is at least one aperture. A sound transmitting membrane is disposed adjacent the one end of the tube such that it covers the aperture for permitting sound to be received within the tube. An ear piece is acoustically connected with the tube to enable an operator to listen to sounds which are carried by the tube. An electrokinetic transducer is disposed adjacent the one end of the tube to produce electric signals indicative of a function of its movement. A signal processing means receives the electrical signals from the electrokinetic transducer and produces a representation which is indicative of a preselected function of the movement of the accelerometer. A display means is connected with the signal processing means to produce a visual display of the representation.

A principal advantage of the present invention is that it produces very accurate measurements of cardiac functions with a noninvasive apparatus. The apparatus has a very high signal to noise ratio.

Another advantage of the present invention is that it collects information which was heretofore not monitored. Yet another advantage of the present invention is that it stores and processes the monitored information.

Yet another advantage of the present invention is that it interfaces readily with currently available medical electronics.

BRIEF DESCRIPTION OF THE FIGURE

The FIGURE is a diagrammatic illustration in partial section of an esophageal stethoscope in accordance with the present invention.

DESCRIPTION OF THE PREFERRED EMBODIMENT

The FIGURE is for the purpose of showing and illustrating a preferred embodiment of the invention only and not the purpose of limiting the invention. The FIGURE shows an electrokinetic transducer means A for generating electrical signals which are indicative of its motion or movement. The motion or movement indicating signals indicate one of acceleration, velocity or displacement or the like but not pressure. The electrokinetic transducer is adapted to be disposed within the esophagus of a patient adjacent the patient's heart. An esophageal positioning means B is provided for selectively positioning the electrokinetic transducer longitudinally or rotationally within the patient's esophagus. A signal processing means C operates on the movement indicating signals from the electrokinetic transducer A to produce representations which are indicative of selected functions of the movement of the electrokinetic transducer A. A display means D is connected with the signal processing means for displaying the representation of preselected functions.

Various electrokinetic transducers may be used in the present invention. The electrokinetic transducer should be of appropriate dimensions to fit within the esophagus of a patient, should have the appropriate range of sensitivity to react to expected cardiac movements, and should be electrically compatible with commonly available processing circuitry. One or several electrokinetic transducers may be disposed along the patient's esophagus. In the preferred embodiment, the electrokinetic transducer is a piezoresistive accelerometer. The accelerometer may have a single axis to measure movement of the heart relative to a single axis. Alternately the accelerometer may be biaxial to measure movement within a plane or triaxial to measure movement in three dimensions. A suitable uniaxial accelerometer has been found to be one manufactured by Entran Devices, Inc. of Little Fails, New Jersey, Model No. EGAL-125R-5D. This accelerometer has a diameter of 3.2 millimeters, a length of 6.9 millimeters, weight of 0.5 grams, nominal full scale acceleration range of plus or minus 5 g (where g is the gravitational acceleration), and a sensitivity of 15 mV/g. A suitable biaxial accelerometer has been found to be one manufactured by Entran Devices, Inc., Model No. EGA2-125R-10D. A suitable triaxial accelerometer has been found to be an Endevco Model 23 PICOTRIAX accelerometer. Accelerometers generally consist of a small mass which is attached to the end of a cantilever beam. Also connected with the cantilevered beam is a piezoresistive or semiconductive strain gauge. The strain gauge undergoes a change in its electrical properties which is related to the acceleration of the device. These piezoresistive accelerometers contain four piezoresistive elements so as to form a Wheatstone bridge.

Alternately, the electrokinetic transducer may be a piezoelectric accelerometer which independently generates a voltage which is directly related to its acceleration. As another alternative, the electrokinetic transducer may produce an electrical signal which is proportional to its velocity. A geophone or seismometer may be used to produce signals which are related to velocity. These devices commonly consist of a permanent magnet which is slidingly disposed in a coil. In response to movement of the device, the magnet slides through the coil. Movement of the magnet relative to the coil generates a velocity related signal. As yet another alternative, microelectronic amplifiers, integrators, and other circuitry may be disposed with the electrokinetic transducer. The integrators can integrate an acceleration related signal to produce a velocity related signal or can integrate a velocity related signal to produce a displacement related signal. Other microelectronic circuitry, such as an analog to digital converter, may also be disposed with the electrokinetic transducer.

The esophageal positioning means B can take numerous forms. Generally it is desired to be able to place the electrokinetic transducer or transducers selectively at different positions within the esophagus. In humans and many other animals, the heart is disposed sufficiently close to the esophagus that the esophagus is moved by the heart's pumping contractions. The aorta also passes close enough to the esophagus to cause the latter to be deflected. It has been found desirable for some measurements to position the electrokinetic transducer adjacent the heart to emphasize movements of the esophagus caused by contractions of the heart. For other measurements it has been found desirable to position the electrokinetic transducer adjacent the aorta to emphasize movement of the esophagus caused by the aorta. Various ways may be used to select the positioning. For example, positioning means B may be used to shift the electrokinetic transducer longitudinally until a peak signal is obtained or until selected features of the output wave form are observed. An electrocardiographic electrode may be attached to the tip of the positioning means. From observations of the esophageal electrocardiogram so obtained, the position of the heart can be ascertained and the electrokinetic transducer located accordingly. The positioning means B may be rotated about its longitudinal axis to maximize the sensitivity of the electrokinetic transducer to the movement. With a biaxial or triaxial accelerometer, for example, the amplitude of the vector sum of the movement components is independent of the rotational position of the accelerometer. Accordingly, the movement related signals can be processed to determine the amplitude of the vector sum and eliminate the rotational positioning step. When the sensitive axes of the accelerometer are known, relative to the orientation of the patient, the amplitude and direction of the resultant vector of the movement may be determined.

In the preferred embodiment the esophageal positioning means B takes the form of a conventional esophageal stethoscope. The stethoscope comprises a lightweight flexible tube 10 which may be made of polyethylene or other suitable material. Disposed adjacent one end of the tube 10 are a plurality of apertures 12 which allow sound to pass into tube 10. The electrokinetic transducer A is securely fastened intermediately along the tube or adjacent one end of tube 10. The electrokinetic transducer can be fastened, for example, frictionally by heat shrinking the tube 10 or the like. If the electrokinetic transducer is smaller in diameter than the tube 10, various adhesives or clips may be used to secure the electrokinetic transducer and the tube together. A sound permeable membrane 14 fits over the one end of tube 10. For clarity of illustration, membrane 14 is shown displaced an exaggerated amount from the end of tube 10. Membrane 14 may be polyethylene, latex, or other material which transmits sound readily. Membrane 14 inhibits fluids from entering the tube through apertures 12 and also provides a closed path for the transmission of sounds. Connected with the other end of the tube are a pair of ear pieces 16 and 18 which are adapted to be placed adjacent the ears of the physician, nurse, or other technician. By listening through the ear pieces to the sound entering the tube at apertures 12, the user can monitor audibly certain caridac functions. Such esophageal stethoscopes are commonly used by anesthetists. If one or more electrokinetic transducers are disposed intermediately along the tube, it is desirable that a passage for sound waves be provided.

A cable of lightweight wires 20 is connected with electrokinetic transducer A. The cable includes the wires for applying any excitation or bias voltage to the electrokinetic transducer or any associated electronics. The cable further comprises wires for carrying the movement indicating signal which is related to the movement of the electrokinetic transducer. An acoustic sealing means 22 allows the electrical signals to be passed out of the tube while inhibiting the acoustic waves within the tube from passing out of the tube or otherwise being attenuated. The acoustic sealing means comprises a small cap which is drilled to accommodate cable 20. An epoxy resin or the like seals the cable with the cap. Alternately cap 22 may include a plug or socket assembly. A suitable esophageal stethoscope has been found to be one which is manufactured by Jelco Laboratories Model HR18003-008418 which is commonly called the "Multiprobe II". This stethoscope, which is sold with a thermistor disposed within tube 10 adjacent the end, is structured to allow an electric cable to pass from the interior to the exterior of the tube. The electrokinetic transducer may replace or supplement the thermistor in the Jelco stethoscope.

Unlike the thermistor which has a pair of wire leads, piezoresistive accelerometers generally have four or more leads. These leads supply an excitation voltage and carry an output acceleration indicating signal for each axis. Piezoelectric accelerometers, geophones and siesomometers which generate an electric potential independently do not require an excitation voltage. However, it is often desirable to have an amplifier or other electronic circuitry disposed with the electrokinetic transducer. The amplified signals are less sensitive to noise acquired in transmitting the signals out of the patient. As yet another alternative, cable 20 may be replaced by attaching a radiotransmitter to the electrokinetic transducer and a radioreceiver to the signal processing means. In lieu of the cable and telemetry systems, other means for transmitting the movement related signals from the electrokinetic transducer to the signal processing means C may be utilized.

Signal processing means C processes the movement related signals from the electrokinetic transducer. The signal processing means is disposed external to the patient. However, by using microelectronics, the signal processing means can be disposed partially or totally within the patient. In the preferred embodiment, the electrokinetic transducer is a piezoresistive accelerometer containing a complete Wheatstone bridge. A bridge driver circuit 30 supplies an electrical potential across the bridge and amplifies the resulting analog output voltage which is the movement indicating signal. With piezoelectric accelerometers, geophones, and seismometers, circuit 30 may be just an amplifier. The amplified signal is a representation indicative of a function of the movement of the electrokinetic transducer. This representation is connected to a display means D to produce a visual representation of the movement which the electrokinetic transducer has undergone. The display means, for example, may be a paper tape strip chart recorder 40 such as a Gould Model 2600. Alternately, the representation of a function of the movement of the electrokinetic transducer may be applied as the y axis signal to an oscilloscope 42 which is swept as a function of time along the x axis. Other display means are also contemplated such as video monitors with the appropriate video processing circuitry, photographic recorders, digital plotters such as Tektronix Model 4662, audio displays, and the like. The circuit 30 and oscilloscope 42 are both available as parts of a Datascope Model P3 and other clinical monitors.

The signal processing means C may process the analog voltage or movement related signal in various ways to produce other functions of the movement of the electrokinetic transducer. For example an integrating circuit 50 may be utilized to integrate the signal with respect to time. This changes a signal which varies with the acceleration of the electrokinetic transducer to a signal which varies with its velocity. Further, a second integrating circuit 52 may integrate the velocity related signal with respect to time to produces a signal representing the displacement of the electrokinetic transducer. Representations of more complex functions of the movement of the electrokinetic transducer may be generated by using a computer 54 or other electronic processing circuitry. Computer 54 is programmed with appropriate mathematical algorithms to generate functions of the movement of the electrokinetic transducer. The computer 54 may be embodied in an Apple II Microcomputer system, Radio Shack TRS-80, or Digital Equipment PDP11/40 having an analog to digital converter system at the input. A switching array 56 switches one or more of the representations with one or more of the display means. The switching means 56 may be a plurality of manual switches, solid state switches, or the like. Taken together a signal processing means C and display means D comprise means for producing a representation which is indicative of a function of the movement of the electrokinetic transducer or accelerometer A.

A memory means 60 may be connected with the switching array for recording in analog or digital format various movement related representations or signals. The data stored in the memory means may be used to produce a permanent record of representations displayed on the oscilloscope 42. Alternately, memory means 60 may store representations for future processing by computer 54. This would enable the same data to be processed with a plurality of mathematical algorithms. Memory means 60 may be a tape recorder, disc storage device, solid state memory, or the like.

It has been found that the acceleration related signals generally take the form of two major oscillation complexes per heartbeat. The first oscillation complex coincides with the isovolumic and rapid ventricular outflow phases of cardiac contraction. The second oscillation complex is associated with aortic backflow and closure of the aortic valve. The peak-to-peak amplitude of the first oscillation complex has been found to vary directly with the inotropic (contractile) state of the heart. The second oscillation complex is believed to measure the shock waves, similar to a water hammer, which travel through the aortic blood when the aortic valve closes. The peak-to-peak amplitude of the second oscillation complex has been found to vary with the effective blood volume in the cardiovascular system. Both of these oscillation complexes and other complexes may be operated on with numerous mathematical algorithms to produce representations indicative of various cardiac functions. Additional complexes may be emphasized with appropriate positionings of the accelerometer.

By appropriate filtering techniques signals similar to heart sounds may be extracted from the acceleration related signals. The signal processing means may contain additional processing circuitry for processing. Other physiological signals, such as the electrocardiogram, systematic arterial and venous pressures and pulmonary artery pressures may be processed in conjunction with signals from the electrokinetic transducer.

The invention has been described with particular reference to the preferred embodiment. Obviously modifications and alterations will occur to others upon reading and understanding the specification. It is my intention to include all such modifications and alterations insofar as they come within the scope of the pending claims or the equivalents thereof.

I claim:

1. An esophageal stethoscope for audibly and electronically monitoring the caridovascular system of a patient, the stethoscope comprising:
    a flexible tube adapted to be disposed in the patient's esophagus;
    at least one aperture disposed adjacent one end of the tube;
    a sound transmitting membrane disposed adjacent said aperture for permitting sound to be received within the tube;

listening means acoustically connected with said tube for enabling an operator to listen to sound within the tube;

at least one electrokinetic transducer means for producing electric signals which indicate the magnitude and direction of a function of the electrokinetic transducer means' motion during positional cycling of the heart, the electrokinetic transducer means being attached near said flexible tube one end;

signal processing means for operating on said electrical signal to produce at least one representation indicative of a preselected function of the motion of the electrokinetic transducer means, said signal processing means being operatively connected with said electrokinetic transducer means; and display means for producing at least one display of said representation, said display means being electrically connected with said signal processing means.

2. The esophageal stethoscope as set forth in claim 1 said electrokinetic transducer means is disposed at the one end of the tube, whereby when partially disposed in the patient's esophagus, longitudinal movement of the tube selects the position of the electrokinetic transducer means relative to the heart or aorta.

3. The esophageal stethoscope as set forth in claim 1 wherein the listening means includes at least one ear piece adapted to be received by an operator's ear, said ear piece being operatively connected with said flexible tube, whereby sounds carried by the flexible tube can be heard by the operator.

4. The esophageal stethoscope as set forth in claim 1 further comprising wires for carrying said electrical signals, said wires being connected with said electrokinetic transducer means and being disposed at least partially within said flexible tube, acoustic sealing means for allowing said electrical signals to pass while inhibiting sound from passing, said acoustic sealing means being operatively connected with the tube and with said wires.

5. The esophageal stethoscope as set forth in claim 1 wherein said signal processing means produces a representation which is indicative of the acceleration of the electrokinetic transducer means.

6. The esophageal stethoscope as set forth in claim 1 wherein said signal processing means produces representation which is indicative of the velocity of the electrokinetic transducer means.

7. The esophageal stethoscope as set forth in claim 1 wherein said signal processing means produces a representation which is indicative of the displacement of the electrokinetic transducer means.

8. The esophageal stethoscope as set forth in claim 1 wherein said electrokinetic transducer means is an accelerometer and the electrical signals are indicative of acceleration.

9. The esophageal stethoscope as set forth in claim 8 wherein said accelerometer is uniaxial.

10. The esophageal stethoscope as set forth in claim 8 wherein said accelerometer is biaxial.

11. The esophageal stethoscope as set forth in claim 8 wherein said accelerometer is triaxial.

12. The esophageal stethoscope as set forth in claim 1 further including a plurality of electrokinetic transducers disposed along the flexible tube, and operatively connected with the signal processing means whereby the signal processing means produces at least one representation indicative of preselected functions of the motion of the plurality of electrokinetic transducer means.

13. The esophageal stethopscope as set forth in claim 7 wherein said electrical signals are indicative of the magnitude and direction of the electrokinetic transducer means' velocity.

14. The method of electronically and audibly monitoring cardiovascular functions of a patient comprising the steps of:

disposing an electrokinetic transducer within the patient's esophagus;

selectively positioning the electrokinetic transducer longitudinally adjacent to the patient's heart to move in response to cardiovascular motion, the electrokinetic transducer producing electrical signals which are indicative of the magnitude and direction of a function of the electrokinetic tranducer's motion during the patient's cardiac cycles;

channeling sound waves from a location near the electrokinetic transducer to a position external to the patient to be audibly monitored; and converting said electrical signals to at least one visual display which is indicative of the electrokinetic transducer's motion, thereby the visual display signifies a cardiovascular function.

15. The method as set forth in claim 14 wherein the electrokinetic transducer is an accelerometer and wherein the electrical signals are indicative of the magnitude and direction of the electrokinetic transducer's acceleration.

* * * * *